(12) United States Patent  
Terrafranca, Jr. et al.

(10) Patent No.: US 7,726,206 B2
(45) Date of Patent: Jun. 1, 2010

(54) FOOT PRESSURE ALERT AND SENSING SYSTEM

(75) Inventors: Nicholas A. Terrafranca, Jr., Laguna Niguel, CA (US); Majid Sarrafzadeh, Anaheim Hills, CA (US); Eric Collins, Mission Viejo, CA (US); Foad Dabiri, Los Angeles, CA (US); Hyduke Noshadi, Northridge, CA (US); Tammara Massey, Los Angeles, CA (US)

(73) Assignees: The Regents of The University of California, Oakland, CA (US); Medisens Wireless, Inc., Mission Viejo, CA (US)

( * ) Notice: Subject to any disclaimer, the term of this patent is extended or adjusted under 35 U.S.C. 154(b) by 151 days.

(21) Appl. No.: 11/934,017

(22) Filed: Nov. 1, 2007

(65) Prior Publication Data
US 2008/0287832 A1    Nov. 20, 2008

Related U.S. Application Data

(60) Provisional application No. 60/864,050, filed on Nov. 2, 2006.

(51) Int. Cl.
*G01D 7/00* (2006.01)
(52) U.S. Cl. ............... 73/862.041; 73/862.042; 73/862.043; 73/862.044; 73/862.045; 73/862.046

(58) Field of Classification Search ............... 73/862.041–862.046
See application file for complete search history.

(56) References Cited

U.S. PATENT DOCUMENTS

| | | | | |
|---|---|---|---|---|
| 4,862,743 A * | 9/1989 | Seitz | ........................... | 73/172 |
| 5,323,650 A * | 6/1994 | Fullen et al. | .................. | 73/172 |
| 5,794,361 A * | 8/1998 | Sadler | ........................... | 36/29 |
| 6,216,545 B1 * | 4/2001 | Taylor | .................. | 73/862.046 |
| 6,807,869 B2 * | 10/2004 | Farringdon et al. | .... | 73/862.046 |
| 6,836,744 B1 * | 12/2004 | Asphahani et al. | .......... | 702/141 |
| 7,526,954 B2 * | 5/2009 | Haselhurst et al. | ............ | 73/172 |
| 2007/0250287 A1 * | 10/2007 | Spector | ...................... | 702/139 |

* cited by examiner

*Primary Examiner*—Max Noori

(57) ABSTRACT

This invention relates to a system that continuously monitors pressure and force on the foot, analyzes and visualizes the pressure and force exerted on said foot in real-time. The invention measures pressure and force applied to a plurality of sensors placed in various points of an orthotic, shoe, shoe lining, insert, sock or sock type device. If the sensors detect pressure or force, the sensors send a signal to a microcomputer processor located in the shoe that subsequently analyzes and sends the data wireless to either a handheld electronic device, a personal computer, an electronic data capture system or a software program. The handheld electronic device or the personal computer then displays the data to an operator of the device or computer instantaneously; while the data capture system or program forwards the information to a handheld device and/or personal computer.

19 Claims, 5 Drawing Sheets

FOOT PRESSURE ALERT AND SENSING SYSTEM

This application claims the benefit of U.S. Provisional Patent Application No. 60/864,050 filed on Nov. 2, 2006, entitled "PRESSURE ALERT SENSING SYSTEM" which is expressly incorporated herein in its entirety.

This invention was made with Government support under Grant No. CNS-0205682 awarded by the National Science Foundation. The Government has certain rights in this invention.

BACKGROUND OF THE INVENTION

1. Field of the Disclosure

The present disclosure generally relates to a system for sensing and alerting a user to pressure and force on his foot.

2. Description of the Related Art

Diabetics and other afflicted people with medical problems can have failures in the nervous system. This could be detrimental to their health since they often do not recognize pain, discomfort, irritation, changes in pressure, swelling, changes in temperature or have an inability to recognize pain, discomfort, irritation, changes in pressure, swelling, or changes in temperature to a sufficient degree to prevent injury, or illness to themselves. This is especially prevalent in the feet of the afflicted person with failure(s) in their nervous system since their feet are susceptible to increased pressure, irritation, changes in pressure, swelling, or changes in temperature while standing, sitting or lying down. Thus, an afflicted person may place too much pressure on a foot or a portion of a foot by physical activity, by standing or even while sitting or lying down. This is problematic because too much pressure on the foot or a portion of the foot could cause increased nerve damage to the foot, destruction of the skin creating an open wound, or a host of other ailments. Thus, there is a need for a low-cost system to alert the user to problematic pressure, and other physiologic and biomechanical changes to their foot or feet along with continuous active monitoring of the changes in pressure and other physiologic and biomechanical changes being applied to their foot or feet.

BRIEF SUMMARY OF THE INVENTION

The present invention is a system for sensing and alerting a user to changes in pressure and force upon a foot during resting, sitting, standing or exercise, like walking, by using footwear having a plurality of primary pressure sensors, a medical node connected to the plurality of primary pressure sensors, and a base station connected to the medical node.

BRIEF DESCRIPTION OF THE DRAWINGS

The exact nature of this invention as well as other objects and advantages thereof will be readily apparent from consideration of the following specification in conjunction with the accompanying drawings in which like numerals designate like parts through the figures thereof and wherein.

DETAILED DESCRIPTION OF THE INVENTION

Figure 1:
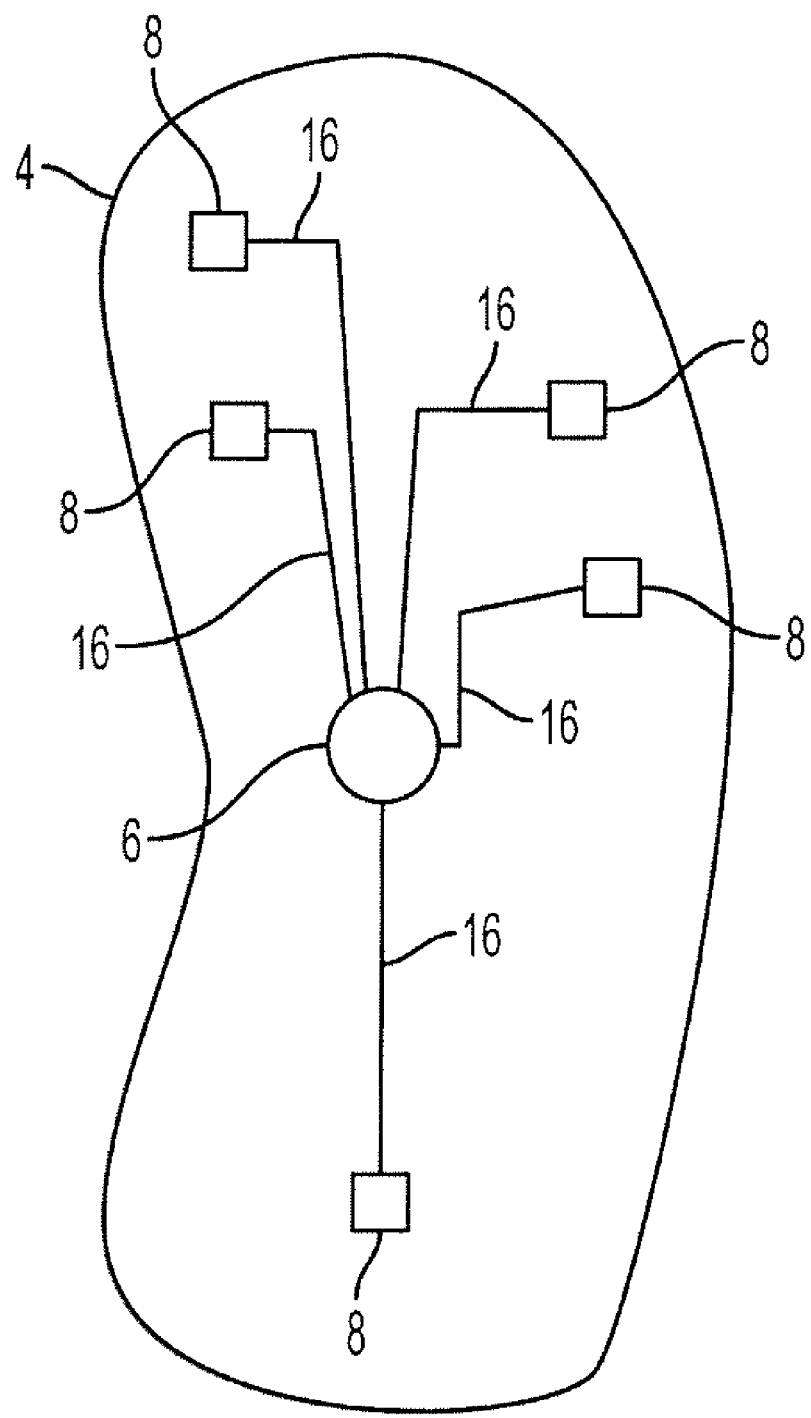
FIG. 1 is a block diagram illustration of footwear with pressure sensors.

FIG. 1 is a diagram illustration of footwear 4 with pressure sensors 8. Footwear 4 may be a removable insert for a shoe. Footwear 4 may also be a sole of a shoe, a sandal, a sock, sock type device, or a boot. Footwear 4 contains a plurality of pressure sensors 8 connected by connections 16 to a medical node 6.

Figure 4:
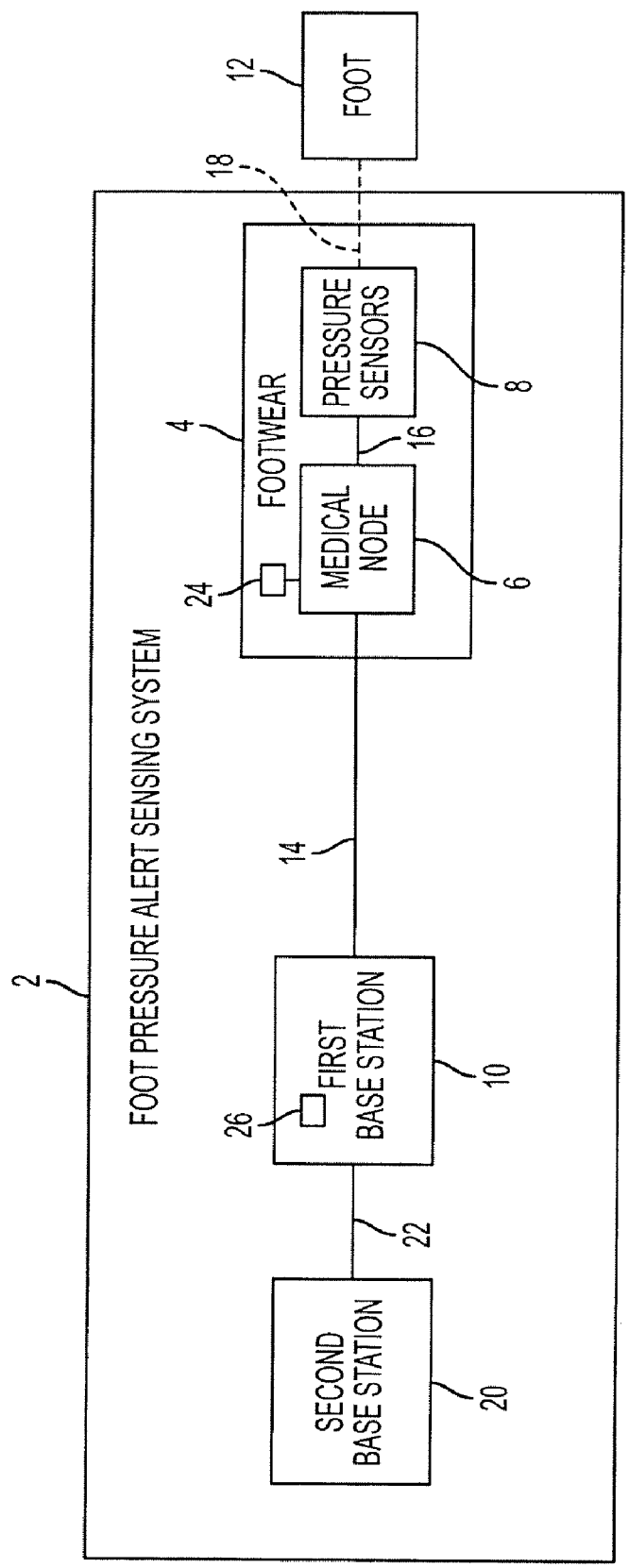
FIG. 4 is a block diagram of a preferred embodiment of a system of the present invention.

Pressure sensors 8 may be resistive pressure sensors, but are not limited to resistive pressure sensors and can be a variety of other types of pressure sensors as well as other physiological and biomechanical sensors. In either case, medical node 6 receives raw data from pressure sensors 8 and generates pressure data for transmission to a first base station 10 (FIG. 4). Although FIG. 1 only depicts five pressure sensors, it is understood that the number of pressure sensors may vary. As many pressures sensors as needed are contemplated.

Medical node 6 can be, for example, a MediSens MedNode™. Medical node 6 has a transmitter (not shown) and a microprocessor (not shown). The microprocessor allows the medical node 6 to process the raw data from pressure sensors 8 to generate the pressure data. The transmitter is used to transmit the pressure data to the first base station 10.

If footwear 4 is a shoe, a sandal, or a boot, medical node 6 does not need to be in the general area where the foot applies pressure on pressure sensors 8. For example, medical node 6 could be in the tongue of the shoe, or on the straps of a sandal, or in the walls and lining of a boot or shoe.

In operation, Pressure sensors 8 sense pressure from a foot placed on them. Where pressure sensors 8 are resistive sensors, the resistance in primary pressure sensors 8 varies as different pressure and/or force is applied to them. Medical node 6 sends current through pressure sensors 8 and determines the pressure at each pressure sensor 8 from the resistance detected.

Figure 2:
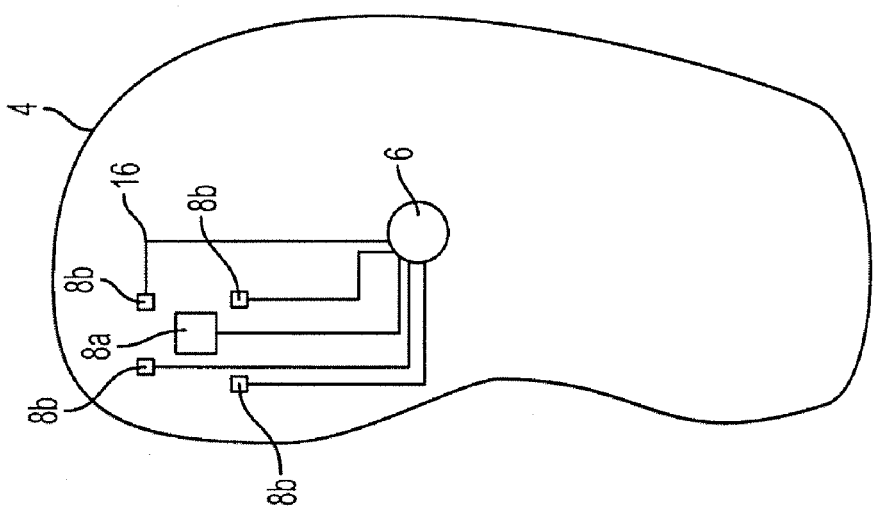
FIG. 2 is a block diagram illustrating an alternative embodiment of the invention as footwear.

FIG. 2 is a block diagram illustrating an alternative embodiment of the invention contained in footwear 4. In FIG. 2, footwear 4 is an insert for a shoe. Instead of only one type of pressures sensor, there are two types of pressure sensors, a primary pressure sensor 8a and secondary pressures sensor 8b. Each primary pressure sensor 8a is surrounded by secondary pressure sensors 8b. When medical node 6 detects that the primary pressure sensor 8a is defective or failing, it activates one or more of the secondary pressure sensors 8b. The medical node can then receive raw data from the secondary pressure sensors 8b instead of primary pressure sensor 8a. This allows the medical node to still receive raw data in the approximate location of the failed primary pressure sensor 8a. The medical node 6 can compensate for the location differences between primary pressure sensor 8a and secondary pressure sensors 8b. Primary pressure sensor 8a will be determined to be defective or failed if it returns substantially the same raw data for a predetermined period of time. Primary sensor 8a will also be determined to be defective or failed if it returns wildly erratic data that varies from high to low in a short period of time or produces useless data.

The secondary pressure sensors 8b are preferably less expensive than the primary pressure sensor 8a. Secondary pressure sensors 8b normally remain dormant and are only activated when necessary, effectively reducing power required. Although FIG. 2 depicts four secondary pressure sensors 8b surrounding a primary pressure sensor 8a, it is understood that the number of secondary pressure sensors 8b could vary. There could be one, two, seven, or even eight or more secondary pressure sensors 8b for each primary pressure sensor 8a. Furthermore, it is unnecessary for every primary pressure sensor 8a to have secondary pressure sensors 8b surrounding it. In addition, is also unnecessary for every primary pressure sensor 8a to have the same number of secondary pressure sensors 8b surrounding it.

It is also contemplated that some or all of the secondary pressure sensors 8b could be activated even when primary pressure sensor 8a has not failed or is not defective. This could be beneficial when more pressure data is necessary such as when a fine analysis is required for pressure on the foot.

Figure 3:
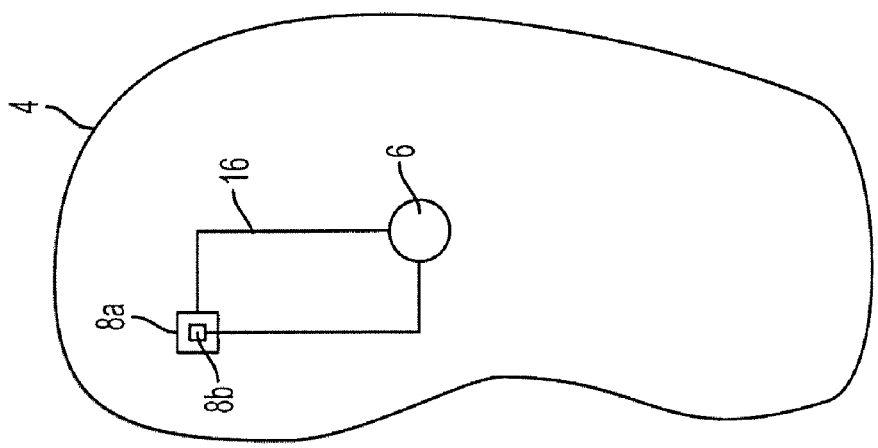
FIG. 3 is a block diagram illustrating another alternative embodiment of the invention as footwear.

FIG. 3 is a block diagram illustrating another embodiment of the invention. In FIG. 3, footwear 4 is an insert for a shoe. Instead of only one type of pressures sensor, there are two types of pressure sensors, primary pressures sensors 8a and secondary pressures sensors 8b. Primary pressure sensor 8a has a secondary pressure sensor 8b placed on top of it. When medical node 6 detects that primary pressure sensor 8a is defective or failing, it activates secondary pressure sensor 8b. Thus, medical node 6 can receive raw data from the secondary pressure sensors 8b instead of primary pressure sensor 8a. This would allow the medical node to still receive raw data in substantially the same location as primary pressure sensor 8a without using primary pressure sensor 8a. However, there would be a depth difference since primary pressure sensor 8a would not be at substantially the same depth as secondary pressure sensor 8b. Medical node 6 can compensate for the depth differences between primary pressure sensor 8a and secondary pressure sensor 8b. Primary pressure sensor 8a may be determined to be defective or failed if it returns substantially the same raw data for a predetermined period of time. Primary sensor 8a can also be determined to be defective or failed if it returns wildly erratic raw data that varies from high to low in a short period of time or produces useless data.

As shown in FIG. 4, the present invention includes a system 2 for sensing and alerting a user to pressure on his foot 12.

Figure 6:
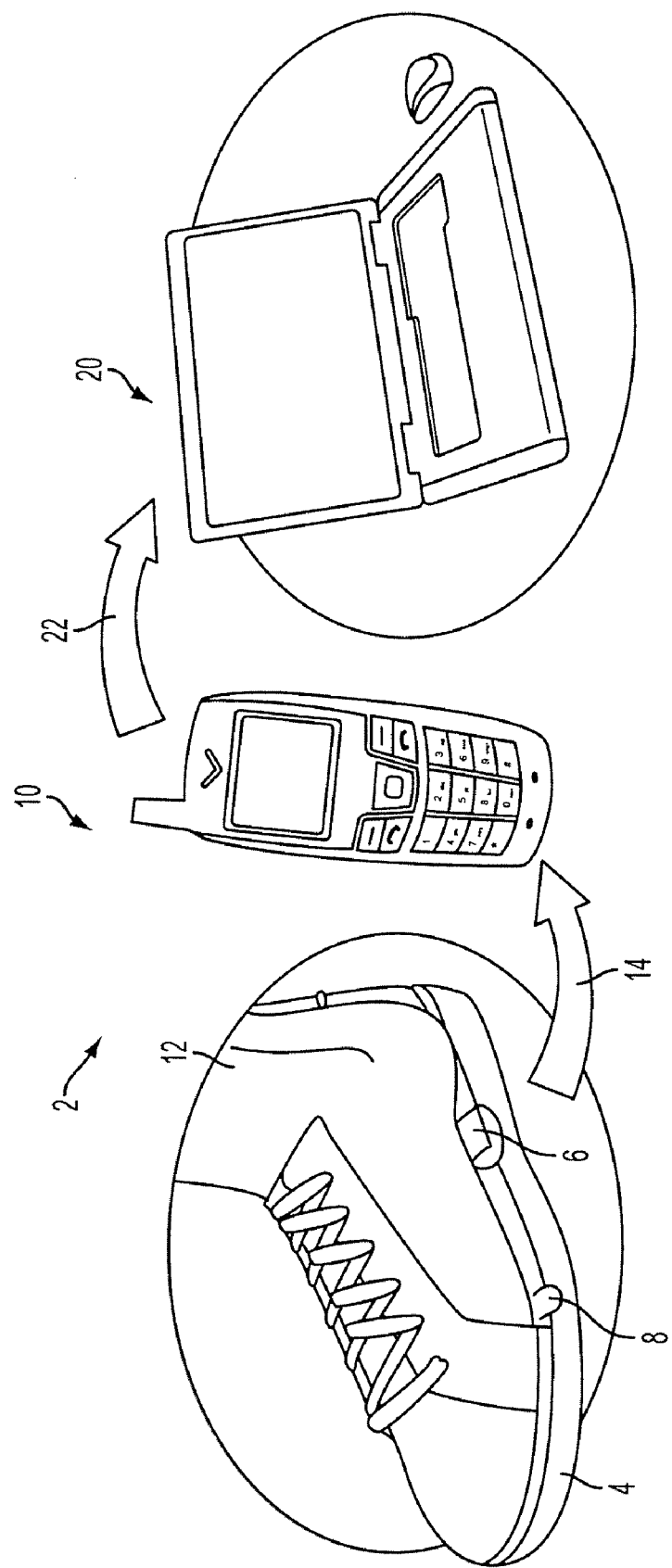
FIG. 6 is a pictorial illustration of a preferred embodiment of a system of the present invention.

Instead of or in addition to medical node 6, a first base station 10 and/or second base station 20 is used to determine if primary pressure sensor 8a is defective or has failed as shown in FIGS. 4 and 6. First base station 10 and/or second base station 20 could also update software within medical node 6 such that medical node 6 could compensate for the difference in depth or location between primary pressure sensor 8a and secondary pressure sensors 8b. Alternatively, first base station 10 and/or second base station 20 would compensate for the difference in depth or location between primary pressure sensor 8a and secondary pressure sensor 8b by altering its analysis of the pressure data received from medical node 6.

Secondary pressure sensor 8b could be cheaper to manufacture, obtain, and/or implement than primary pressure sensor 8a. Secondary pressure sensor 8b could also remain dormant and only be active when activated so as to not unnecessarily draw power from battery 24. Although FIG. 3 depicts a single secondary pressure sensor 8b on top of primary pressure sensor 8a, it is understood that the number of secondary pressure sensors 8b could vary. Thus, there could be one, two, seven, or even eight or more secondary pressure sensors 8b for each primary pressure sensor 8a. Furthermore, not every primary pressure sensor 8a needs to have a secondary pressure sensors 8b on top of it. In addition, it is unnecessary for every primary pressure sensor 8a to have the same number of secondary pressure sensors 8b on top of it. Furthermore, the location of the secondary sensor 8b could vary, such that it could be on the bottom of the primary pressure sensor 8a.

It is also contemplated that some or all of the secondary pressure sensors 8b could be activated even when primary pressure sensor 8a has not failed or is not defective. This could be beneficial when more pressure data is necessary such as when a fine analysis is used for the pressure on his foot.

System 2 has a footwear 4 such as one illustrated in FIG. 1, 2, or 3. Footwear 4 has a plurality of pressure sensors 8 which receive pressure when the foot 12 physically contacts 18 the pressure sensors 8. The plurality of pressure sensors 8 are connected to medical node 6 through connection 16. A battery 24 is connected to medical node 6. Although only one footwear or shoe 4 is shown, the present system has equal application to more than one shoe.

Battery 24 preferably has a minimized physical presence and weight. Battery 24 can be a rechargeable and removable battery. In the situation where battery 24 is a rechargeable and removable battery, medical node 6 can detect when battery 24 is low on power such that it needs to be removed and recharged. Furthermore, battery 24 can also be recharged through the movements of footwear 4 such as when footwear 4 is inserted in a shoe or is part of a shoe. In such a situation it is unnecessary for battery 24 to be removable. Although not shown, a back-up battery can also be included.

First base station 10 is connected to footwear 4 by a connection 14. Connection 14 is a wireless connection in FIG. 4, but could also be a wired connection. As a wireless connection, connection 14 could be an Internet connection, a Bluetooth connection, a telephone signal, etc.

First base station 10 is a computer, but it can also be any other type of electronic device such as a mobile phone, a blackberry, an iPhone, an iPod, etc. First base station 10 can also be an intermediate communication module such as a monitoring station designed to receive and transmit pressure data which allows the medical node 6 to only transmit pressure data to first base station 10. If first base station 10 is an intermediate communication module, it may have a more powerful transmitter to relay the pressure data to a more distant location to a second base station 20. Battery 24 connected to medical node 6 may thus be reduced in size, reducing costs, and allowing for a greater degree of portability of footwear 4.

First base station 10 preferably has a storage device 26 to store the pressure data from the medical node 6. First base station 10 can then use and/or analyze the pressure data to generate useful analysis of the pressure data in the form of X-Y charts based on time and pressure. This could be helpful in detecting problems the user has with placing pressure on his feet and allowing the user to correct such problems.

Figure 5:
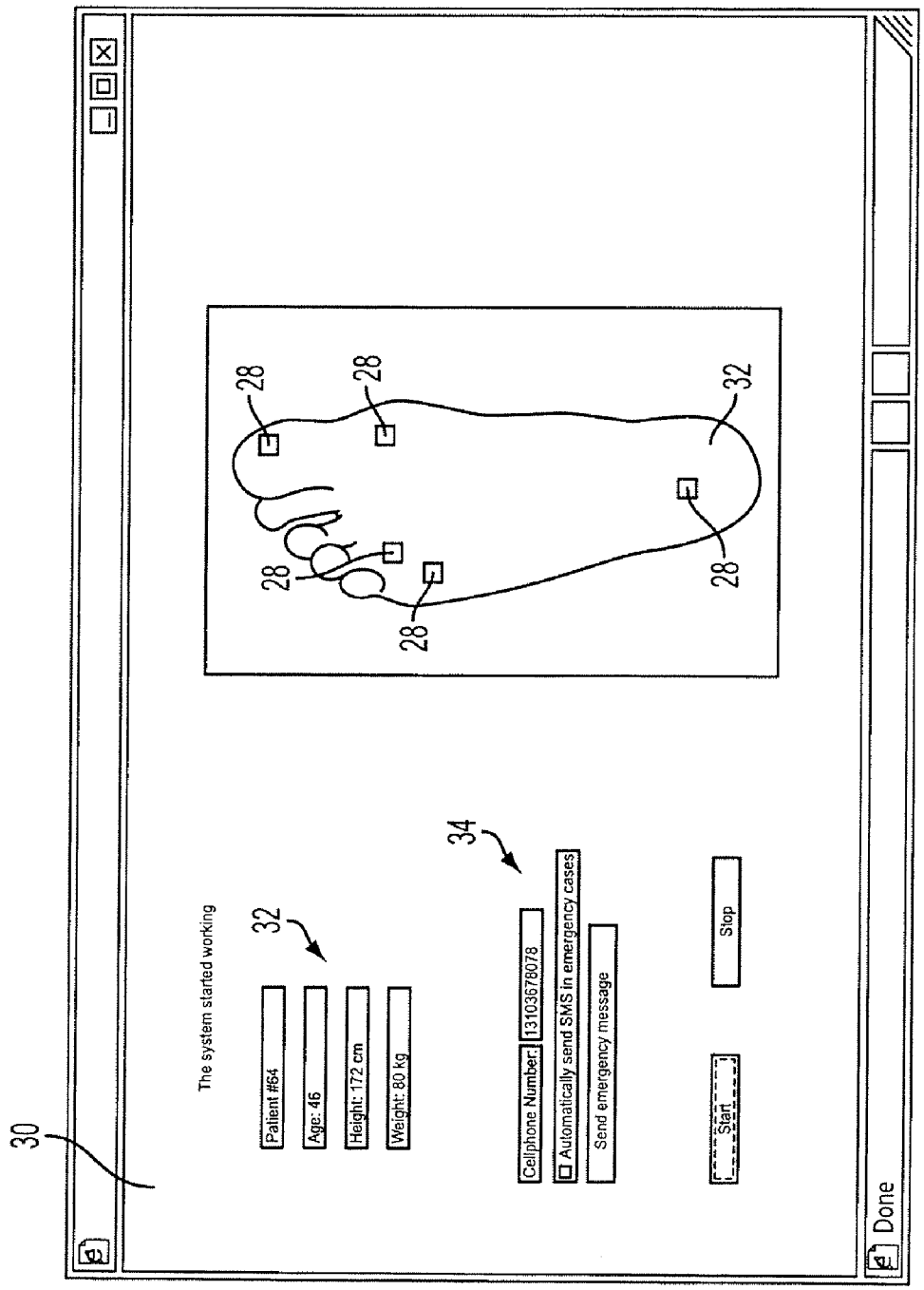
FIG. 5 is an abstract illustration of a screen of a base station.

Furthermore, first base station 10 could also have an optional display 30 as shown in FIG. 5.

A second base station 20 may be connected to the first base station 10 by a connection 22. Second base station 20 is preferably a computer. It can also be any other type of electronic device such as a mobile phone, a blackberry, an iPhone, an iPod, etc. Second base station 20 is preferably located remotely from first base station 10. The user of first base station 10 need not be the same as the user for the second base station 20. The user of the second base station 20 could be a doctor, physician, nurse, or family member, for example. This allows different people to access the pressure data generated by medical node 6.

In operation, foot 12 from a user is placed over footwear 4. The foot 12 applies pressure to footwear 4 through physical contact 18 with the pressure sensor, such as when the user steps on footwear 4. Pressure sensors 8 (8a and/or 8b) detect the pressure being applied by foot 12 and transmit the raw data to medical node 6. Medical node 6 receives the raw data from pressure sensors 8 (8a and/or 8b) through connection 16 and generates pressure data from the raw data.

Medical node 6 transmits the pressure data to a first base station 10 through connection 14. First base station 10 receives the pressure data from medical node 6 and analyzes the pressure data. First base station 10 can also optionally transmit the pressure data to second base station 20 through connection 22.

When first base station 10 analyzes the pressure data, it may generate an event alert if a predetermined event occurs. A predetermined event occurs when the pressure data indicates that there is pressure above a predetermined level and for longer than a predetermined time period at one or more of the primary pressure sensors. This potentially prevents a user from putting too much pressure on a certain portion of his foot 12, preventing the user from cutting off circulation to a portion of his foot and/or destroying the skin and other surrounding tissue structures of the foot. The present invention is designed to help prevent serious damage to a foot structure leading to possible amputation of his foot or afflicted extremity.

When first base station 10 generates an event alert, it sends a text message, page, voice mail or e-mail to the user and/or caregiver. First base station 10 can also send auditory signals in addition to other visual or vibratory signals to the user and/or caregiver.

As shown in FIG. 5, first base station 10 has an optional display 30 showing a simulated image 32 of a user's foot. Points 28 correspond to locations of primary pressure sensors 8 (8a and/or 8b). When pressure is applied on foot 12 and is detected by primary sensors 8 (8a and/or 8b), points 28 may change colors to indicate the amount of pressure on a user's foot 12. The color of points 28 could be the foot's natural color if there is normal pressure and/or force, but the color of points 28 could change to red if there is high pressure and/or force.

Display 30 also indicates the user's information such as his ID number, age, height, weight, etc. It also has a section 34 to allow the user to input his phone numbers and/or check to see if the user wants to automatically send a text message, or other alert if there is a predetermined event. Section 34 of display 30 can also be used to input multiple phone numbers such as the mobile phone number of a doctor or family member. Section 34 may also be used to input a user's e-mail address or other e-mail addresses in which case first base station 10 can automatically send an e-mail to the appropriate person when there is a predetermined event. Section 34 may also be used to generate event alerts to a variety of other devices such as a personal digital assistant, iPod, or other handheld or worn electronic device when a predetermined event occurs.

First base station 10 may also be used to alter the functionality of medical node 6 and pressure sensors 8 (8a and/or 8b). For example, the following alterations to medical node 6 can be performed:

Reconfiguration of data acquisition procedure like change of sampling rate;

Alteration between sensors: switch to primary pressure sensors 8a or secondary pressure sensors 8b as shown in FIGS. 2 and 3;

Reconfiguring fault tolerant coding techniques: Switch to more/less reliable coding of the sample data for transmission to first base station 10;

Change precision and accuracy by adjusting supply voltage and quantization factors in an Analog to Digital Converter ("ADC");

Rerouting the links among the sensors and transceivers; and

Modification in raw data processing including but not limited to filtering and noise reduction.

When first base station 10 is communicating with medical node 6 to retrieve data or calibrate medical node 6, first base station 10 and medical node 6 can communicate at various levels of security. While it is important to protect medical data, it is also important to minimize cost and realize the limitations of battery 24. Thus, first base station 10 can choose the sophistication of the security used when communicating with medical node 6.

For example, if there are four levels of security possible, with the first security level being the lowest form of security and the fourth security level being the highest form of security, if the situation is urgent, first base station 10 could choose the first security level or lowest form of security. However, if the situation is not urgent, first base station 10 could choose the fourth security level or the highest form of security. A non-urgent situation could be when the user is walking around performing ordinary daily tasks. In that case, the desired security level would be high since the user would want to protect his medical data but has no pressing need to retrieve the pressure data as soon as possible. An urgent situation could be when there is a predetermined event that requires immediate attention. In that case, the desired security level would be minimal since although the user would want to have some form of protection for his medical data, the need to retrieve the pressure data and act on it as soon as possible is more important.

In one contemplated embodiment, the first level of security is plaintext. The second level of security would be authentication only and a type of cipher block chaining would compute and verify the message integrity. The third level of security would have authentication and encryption with Skipjack cryptography. The fourth level of security would have authentication and encryption with RC5 cryptography. It is contemplated that the authentication and encryption necessary for each level of security is changeable as well as having more or less levels of security.

The components of the present invention including first base station 10, second base station 20, medical node 6, and/or primary pressure sensors 8 (8a and/or 8b) can be calibrated. To calibrate the present invention, two types of pressure data are used. First is the total amount of pressure applied to a foot. Second is the pressure sensed at designated points of the foot such as points where the foot touches the shoe or ground. The pressures sensed can be a variety of types of forces such as shear force for example. This force data will be used to measure and assess the correct pressure. Every time the user uses footwear 4 for the first time, the present invention will calibrate and get the initial pressure and balanced condition's pressure, such as at designated points of the foot, and the whole foot.

The total pressure sensed of both feet in the calibration state will be used as a baseline for comparison purposes in the future detection of pressure on the foot. In those instances where only one foot is involved baselines, for comparison, will be derived from the average norm of similar patients with the same condition, as well as from the patient's previous calibrated states. When the calibration is done, the data is consistently received from medical node 6, the pressure is computed and a report of the possible repercussions is generated, based on the following:

1.) Patient is not moving: In this case the system will take the whole pressure sensed from both feet. By comparing the relation between the amount of total pressure applied by each foot, or the average norm in the case of one foot, and the pressure active area with the calibrated data, the system can detect if the foot with the higher pressure is projecting the correct amount of pressure or not, or if both feet are being subjected to excessive pressure as in the case of excessive lower extremity edema. For example, if the user is leaning to the left, he puts all of his weight on the left foot while the right foot is still on the ground. In this case the amount of pressure applied to the right foot will be less than normal but the active area is unchanged. However the left medical node will sense more pressure, and the active area will be focused in the outer side of the foot. In this case the present invention will compute the pressure based on the active area in each shoe and will compare the results with the calibration result. It will then make a decision, such as whether a predetermined event has occurred, based on the comparison.

2) Patient is moving: Movement can be detected as extreme changes in the locality of the pressure applied to the foot. For example, pressure will normally be from the right foot to left foot and from the heel to the toe. The present invention will analyze the data in fixed time intervals. In each time interval the present invention will analyze pressure data received from each footwear 4 similar to when the patient is not moving and first places the footwear 4 or shoe on.

Calibration can also be done automatically on medical node 6 each time the shoelace tightness is altered or other events which might alter the analysis of pressure data. Also, since the detected pressure is a function of human mass and the area where the force is applied, the system can also be used for measuring the user's weight.

As shown in FIG. 6, a foot 12 places pressure on footwear 4. Pressure sensors 8 (8a and/or 8b) transmit raw data to medical node 6, which in turn generates pressure data and transmits it to base station 10 via a connection 14. In this embodiment, base station 10 is a mobile phone and connection 14 is a Bluetooth connection. Base station 10 then transmits the pressure data to base station 20 through a wireless connection 22. In this embodiment, base station 20 is a laptop computer and connection 22 is a cellular connection. However, connection 22 can be a variety of other types of wireless connections such as a satellite connection.

Although not shown, footwear 4 could also have temperature sensors connected to medical node 6 to ascertain the temperature of a foot. Alternatively, the pressures sensors 8 (8a and/or 8b) could be configured to sense temperature, too. In addition, footwear 4 could have sensors for the heart rate of a user, galvanic skin response, precipitation, or oximetry, for example. Footwear 4 could also contain an accelerometer.

Obviously many modifications and variations of the present invention are possible in light of the above teachings. It is therefore to be understood that within the scope of the appended claims the invention may be practiced otherwise than as specifically described.

We claim:

1. Footwear capable of sensing and alerting a user to pressure upon a foot comprising:
   a plurality of primary pressure sensors located in the footwear;
   a plurality of secondary pressure sensors located in the footwear, and adapted to be activated only when one or more of the primary pressure sensors are defective; and
   a medical node located in the footwear connected to the primary pressure sensors and the secondary pressure sensors, the medical node receiving data from the primary pressure sensors and the secondary pressure sensors, processing the data to generate pressure data, and transmitting the pressure data.

2. The footwear of claim 1 wherein the medical node transmits the pressure data to a base station.

3. The footwear of claim 2 wherein the base station analyzes the pressure data and generates an event alert if a predetermined condition occurs.

4. The footwear of claim 3 wherein a predetermined condition occurs when the pressure data indicates that there is pressure above a predetermined level and for longer than a predetermined time period at one or more of the plurality of primary pressure sensors.

5. The footwear of claim 3 wherein the event alert includes a media alert to an electronic device.

6. The footwear of claim 3 wherein the event alert includes a text message to a mobile phone.

7. The footwear of claim 2 wherein the base station calibrates the medical node and the pressures sensors.

8. The footwear of claim 1 wherein a rechargeable battery is connected to the medical node.

9. A system for sensing and alerting a user to pressure upon a foot comprising:
   footwear containing a plurality of primary pressure sensors, a plurality of secondary pressure sensors and a medical node connected to the primary pressure sensors, and the secondary pressure sensors, one or more of the secondary pressure sensors being activated only when one or more of the primary pressure sensors become defective, the medical node receiving data from the primary pressure sensors and the secondary pressure sensors and processing the received data to generate pressure data; and
   a first base station connected to the medical node to receive the pressure data, the first base station adapted to analyze the pressure data and generate an event alert when the pressure data indicates that there is pressure above a predetermined level or for longer than a predetermined time period at one or more of the pressure sensors.

10. The system of claim 9 wherein the first base station includes a data storage module to store the pressure data received from the medical node.

11. The system of claim 9 wherein the event alert includes a media alert to an electronic device.

12. The system of claim 9 wherein the event alert includes a text message to a mobile phone.

13. The system of claim 9 wherein the base station calibrates the medical node, the primary pressures sensors, and the secondary pressure sensors.

14. The system of claim 9 wherein a rechargeable battery is connected to the medical node.

15. The system of claim 9 further comprising a second base station connected to the first base station.

16. The system of claim 9 wherein the base station communicates with the medical node with a variable level of security depending on a desired security level.

17. The system of claim 9 wherein the predetermined event occurs when the pressure data indicates that there is pressure above a predetermined level or for longer than a predetermined time period at one or more of the plurality of pressure sensors.

18. The system of claim 9 wherein the footwear is an insert for a shoe.

19. The system of claim 9 wherein the footwear is a sole of a shoe.

\* \* \* \* \*